United States Patent
Ninomiya et al.

(10) Patent No.: US 7,087,800 B2
(45) Date of Patent: Aug. 8, 2006

(54) PROCESS FOR PRODUCING A POLYOL

(75) Inventors: Teruyuki Ninomiya, Okayama-ken (JP); Toshio Watanabe, Okayama-ken (JP); Atsushi Iwamoto, Okayama-ken (JP); Soemu Miyashita, Okayama-ken (JP); Masafumi Watanabe, Okayama-ken (JP)

(73) Assignee: Mitsubishi Gas Chemical Company, INC, Tokyo (JP)

(*) Notice: Subject to any disclaimer, the term of this patent is extended or adjusted under 35 U.S.C. 154(b) by 793 days.

(21) Appl. No.: 09/874,276

(22) Filed: Jun. 6, 2001

(65) Prior Publication Data

US 2002/0007095 A1  Jan. 17, 2002

(30) Foreign Application Priority Data

Jun. 27, 2000 (JP) ............................. 2000-192468
Jun. 27, 2000 (JP) ............................. 2000-192469
Jun. 27, 2000 (JP) ............................. 2000-192470
Jun. 27, 2000 (JP) ............................. 2000-192471

(51) Int. Cl.
*C07C 27/26* (2006.01)

(52) U.S. Cl. ...................... 568/854; 568/853
(58) Field of Classification Search ............... 568/853, 568/854
See application file for complete search history.

(56) References Cited

U.S. PATENT DOCUMENTS 3,956,406 A  *  5/1976  Palmer et al. ............... 568/854
5,948,943 A  *  9/1999  Supplee et al. ............. 568/854

FOREIGN PATENT DOCUMENTS

EP  0 708 073 A1  4/1996
JP  61-93133 A  5/1986

* cited by examiner

*Primary Examiner*—Elvis O. Price
(74) *Attorney, Agent, or Firm*—Antonelli, Terry, Stout and Kraus, LLP.

(57) ABSTRACT

A process for producing a polyol by reacting an aliphatic aldehyde with formaldehyde in the presence of a basic catalyst, which comprises a step of concentration which comprises removing water and unreacted formaldehyde from a reaction liquid by distillation; a step of extraction which comprises extracting the polyol from a concentrated reaction liquid with an extracting reagent; a step of washing with water which comprises washing an extract liquid with water and separating the liquid into an oil layer containing the polyol and an aqueous layer; wherein by useing an specific aliphatic aldehyde as the extracting agent and recovering the extracting reagent from the oil layer containing the polyol after adjusting pH of the oil layer, a high purity polyhydric alcohol can be obtained at a high yield with suppressed formation of byproducts such as acetal compounds and aldol compounds.

13 Claims, 1 Drawing Sheet

PROCESS FOR PRODUCING A POLYOL

BACKGROUND OF THE INVENTION

1. Field of the Invention

The present invention relates to a process for producing a polyol which is useful as a material for polyester resins, alkid resins, polyurethane resins, polycarbonate resins, plasticizers, lubricants, surfactants, base materials for cosmetics, and reactive monomers.

2. Description of the Related Art

In general, a process for producing a polyol includes a step of reaction, a step of extraction of the polyol from the reaction product liquid, a step of separation of the extracting reagent and a step of purification of the product by distillation. In the step of reaction, it is known that an aliphatic aldehyde and formaldehyde can be reacted in two steps comprising the aldol condensation and the cross-Cannizzaro reaction, successively (U.S. Pat. No. 3,935,274 and Japanese Patent Application Laid-Open No. 61(1986)-18741).

The reaction product liquid is concentrated, where necessary, and separated into salts of formic acid and the polyol in the step of extraction in accordance with a conventional process of extraction (Japanese Patent Application Publication No. Showa 52(1977)-30486 and Showa 44(1969)-10767). Then, in the step of separation of the extracting reagent, the extracting reagent is separated from an extract liquid containing the polyol in accordance with a distillation process. The obtained crude polyol is purified in the step of purification by distillation. For example, when the extraction is conducted using a solvent such as an alcohol and a ketone as the extracting reagent and then the extracting agent is separated, 0.5 to 2% of a salt of formic acid remains in the crude polyol. When the salt of formic acid is heated during purification of the crude polyol by distillation, the salt is converted into a basic compound. The formed basic compound triggers heat decomposition of the polyol. Therefore, the crude polyol containing the salt of formic acid cannot be purified by distillation without any treatments. It is generally conducted that the salt of formic acid is deactivated by adding an acid such as phosphoric acid so that the heat decomposition of the polyol is suppressed (Japanese Patent Application Laid-Open No. Showa 63(1988)-139141).

Recently, polyols are used in a wide variety of fields. In particular, when polyols are used as the raw materials for resins curable by ultraviolet light, polyols having a more excellent quality than conventional products are required. However, the quality of polyols produced by distillation in accordance with a batch process fluctuates among fractions. Therefore, to satisfy the requirement for the excellent quality, it is necessary that the quality be stabilized by conducting the distillation in accordance with a continuous process.

As described above, when the reaction product liquid is treated by extraction using an alcohol or a ketone as the extracting reagent in accordance with a conventional process, an acid is added to the reaction product liquid to deactivate a salt of formic acid since 0.5% or more of the salt of formic acid remains in the crude polyol. In this case, when the purification by distillation is conducted in accordance with a continuous process, salts of the acid such as salts of phosphoric acid are precipitated at the inside and at the bottom portion of the distillation column and clogging takes place. Therefore, a stable continuous operation cannot be achieved. Thus, the distillation must be conducted in accordance with the batch operation and fluctuation in the quality of the product is inevitable. Moreover, when the reaction product liquid is treated by extraction with an alcohol or a ketone, the yield of the extracted polyol is small and the cost of production increases. The quality of the salt of formic acid as a byproduct also deteriorates.

When an aliphatic aldehyde is used as the extracting reagent, the yield of the extracted polyol increases and the fraction of the removed salt of formic acid also increases. For example, a process in which butyraldehyde is used as the extracting reagent is described in Japanese Patent Application Publication Heisei 4(1992)-17169. In accordance with this process, the amount of a salt of formic acid remaining in the extracted and separated polyol can be suppressed to 0.3% or less. However, although the continuous distillation of this crude polyol can be conducted, a great amount of acetals are formed from the polyol and the aldehyde used as the extracting reagent in distillation under an atmospheric pressure for separating the extracting reagent since aldehyde which is used as the extracting reagent is very reactive itself. For example, when the aliphatic aldehyde is normal-butyraldehyde (referred to as NBAL, hereinafter) and the polyol is trimethylolpropane (referred to as TMP, hereinafter), TMP-NBAL acetal expressed by formula (iii):

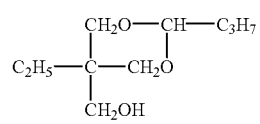

(iii)

is formed as a byproduct. NBAL aldol expressed by formula (iv):

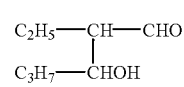

(iv)

is formed as another byproduct by the reaction between NBAL molecules. Moreover, methanol and 2-alkenol expressed by formula (v):

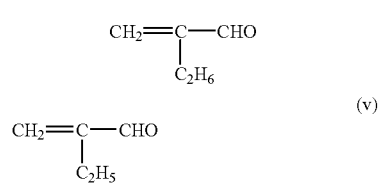

(v)

(v)

which is an intermediate reaction product of methanol and TMP contained in the reaction product liquid is extracted. These compounds are separated and recovered together with the extracting reagent during separation of the extracting reagent.

When distillation is conducted at a low temperature under a reduced pressure, the fraction of the recovered solvent decreases although acetals are not formed as byproducts, and this process cannot be used practically.

When the recovered aldehyde is repeatedly used as the extracting reagent, these impurities are accumulated and adversely affect the extraction. The quality of the polyol is also adversely affected. To overcome this problem, the extracting reagent may be regenerated by distillation.

However, the regeneration requires complicated operations and is industrially disadvantageous.

The amount of the salts of formic acid remaining in the extract liquid may be decreased by washing the extract liquid with water after the extraction. In this case, the aqueous layer separated in the step of washing with water contains the polyol in some amount and it is desirable that the washing water is reused.

In recycling the washing water to the step of extraction, when the aqueous layer separated in the step of washing with water is mixed with the concentrated reaction liquid to be treated by the extraction without any treatments and used for the extraction, the concentration of water in the liquid to be treated by the extraction increases and the efficiency of the extraction decreases. The reaction product liquid is therefore concentrated to prevent the decrease in the efficiency of the extraction. However, when the reaction product liquid is concentrated excessively (a concentration of the salt of formic acid of 25% or greater), problems such as clogging of piping due to separation of the salt of formic acid take place and the operation becomes difficult.

On the other hand, when the washing water is recycled to the step of concentration of the reaction product liquid without any treatments, in other words, when the washing water containing the extracting reagent is recycled, degeneration of the extracting reagent and side reactions of the extracting reagent with the polyol take place.

SUMMARY OF THE INVENTION

Under the above circumstances, the present invention has a first object of providing a process for producing a polyol by reaction of an aliphatic aldehyde and formaldehyde in the presence of a basic catalyst, in accordance with which acetal compounds and aldol compounds are formed only in small amounts and a high purity polyol is produced at a high yield even when the aliphatic aldehyde is used as the extracting reagent, recovered after being used for the extraction and reused for the extraction.

The present invention has a second object of providing a process for producing a polyol by reaction of an aliphatic aldehyde and formaldehyde in the presence of a basic catalyst, in accordance with which, when the polyol of the object compound is separated from the reaction product liquid by extraction, a high purity polyol is efficiently separated from a salt of formic acid while accumulation of impurities in an extracting reagent is prevented.

The present invention has a third object of providing a process for producing a polyol by reaction of an aliphatic aldehyde and formaldehyde in the presence of a basic catalyst, in accordance with which the polyol and a salt of formic acid are efficiently separated by a stable operation.

As the result of the intensive studies by the present inventors to overcome the above problems, it was found that, with respect to the first object, a high purity polyol can be obtained with suppressed formation of byproducts when a specific aliphatic aldehyde is used as the extracting reagent and the extracting reagent is recovered after pH of the extract liquid is suitably adjusted.

The first invention provides a process for producing a polyol by reacting an aliphatic aldehyde represented by formula (i):

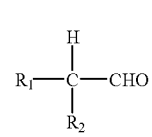

wherein $R_1$ and $R_2$ each represent hydrogen atom or an aliphatic alkyl group having 1 to 6 carbon atoms, with formaldehyde in a presence of a basic catalyst, which process comprises (1) a step of concentration which comprises removing water and unreacted formaldehyde from a reaction liquid by distillation; (2) a step of extraction which comprises extracting the polyol from a concentrated reaction liquid with an extracting reagent; and (3) a step of washing with water which comprises washing an extract liquid with water and separating the liquid into an oil layer containing the polyol and an aqueous layer; wherein an aliphatic aldehyde represented by formula (ii):

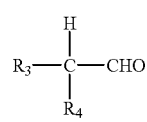

wherein $R_3$ represents hydrogen atom or an aliphatic alkyl group having 1 or 2 carbon atoms and $R_4$ represents an aliphatic alkyl group having 1 to 5 carbon atoms is used as the extracting reagent, and the extracting reagent is recovered after adjusting pH of the oil layer containing the polyol which is separated in the step of washing with water.

With respect to the second object, it was found that an efficient extraction can be achieved and accumulation of impurities in an extracting reagent is suppressed when the extraction is conducted using as the extracting reagent the same aliphatic aldehyde as that used as a raw material of the reaction and a portion of the recovered extracting reagent is used as the raw material of the reaction.

The second invention provides a process for producing a polyol described in the first invention, wherein a same aliphatic aldehyde as the aliphatic aldehyde used as a raw material of the reaction is used as the extracting reagent and at least a portion of the recovered extracting reagent is used as the raw material of the reaction.

With respect to the third object, it was found that an efficient and stable operation can be achieved when washing water of the extract liquid is recycled to the step of extraction after the extracting reagent and a portion of water are removed or to the step of concentration after the extracting reagent is removed.

The third invention provides a process for producing a polyol described in the first invention, wherein the extract liquid is washed with water using a decanter in the step of washing with water, the extracting reagent in a separated aqueous layer is removed by distillation and water obtained from a bottom of a distillation column in the distillation is recycled to the step of concentration; and a process for producing a polyol described in the first invention, wherein the extract liquid is washed with water using a decanter in the step of washing with water, the extracting reagent and a portion of water in a separated aqueous layer are removed by distillation and a liquid obtained from a bottom of a distillation column in the distillation is recycled to the step of extraction.

BRIEF DESCRIPTION OF THE DRAWINGS

In FIG. 1, 1 means a reactor, 6 means a concentration column, 9 means an extractor, 13 means a tank for washing with water, 17 means a column for recovering an extracting reagent and 18 means a column for removing an extracting reagent.

DESCRIPTION OF THE PREFERRED EMBODIMENTS

Figure 1:
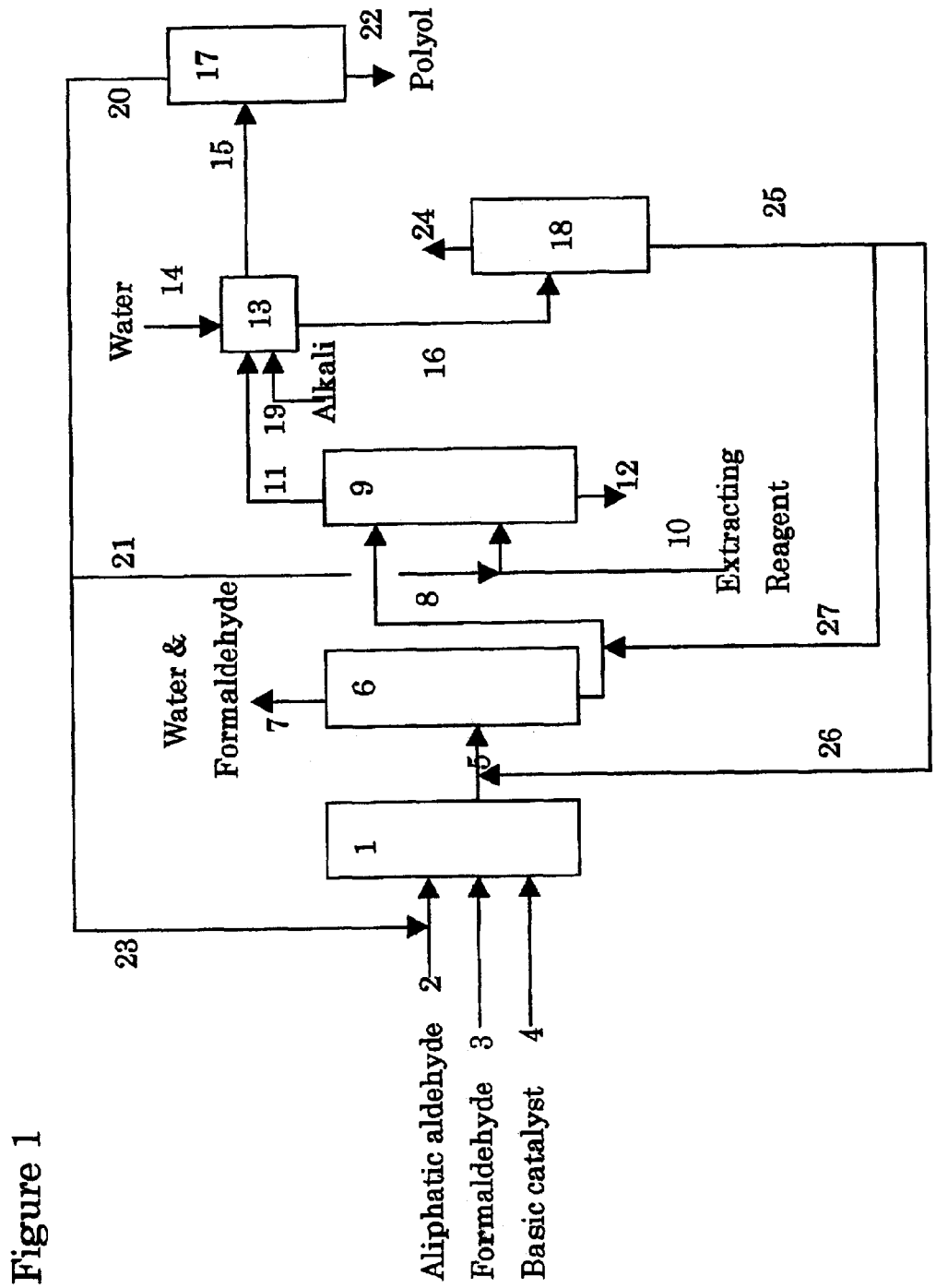
FIG. 1 shows a diagram describing the steps in the process for producing a polyol of the present invention.

As the raw material in the process for producing a polyol of the present invention, an aliphatic aldehyde represented by the following formula (i) is used:

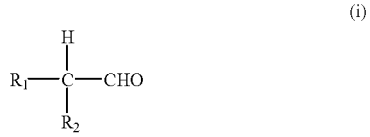

(i)

wherein $R_1$ and $R_2$ each represent hydrogen atom or an aliphatic alkyl group having 1 to 6 carbon atoms Examples of the aliphatic aldehyde used as the raw material include normal-butyraldehyde (referred to as NBAL, hereinafter) represented by formula (i) in which $R_1$ represents ethyl group and $R_2$ represents hydrogen atom and isobutyraldehyde (referred to as IBAL) represented by formula (i) in which $R_1$ and $R_2$ both represent methyl group. A polyol corresponding to the aliphatic aldehyde used as the raw material is produced from the aliphatic aldehyde. For example, trimethylolpropane (referred to as TMP, hereinafter) is produced from NBAL and neopentyl glycol (referred to as NPG) is produced from IBAL.

As formaldehyde, an aqueous solution of formaldehyde or solid formaldehyde may be used. The amount of formaldehyde is different depending on the polyol to be produced. For example, when TMP is produced from NBAL, it is preferable that the amount of formaldehyde is 3.0 to 6.0 moles and more preferably 3.05 to 4.0 moles per 1 mole of NBAL (the theoretical ratio of the amounts by mole: 3.0). When NPG is produced from IBAL, it is preferable that the amount of formaldehyde is 2.0 to 5.0 and more preferably 2.05 to 2.2 moles per 1 mole of IBAL (the theoretical ratio of the amounts by mole: 2.0).

In the present invention, as the basic catalyst in the aldol condensation and the cross-Cannizzaro reaction of the aliphatic aldehyde and formaldehyde, amines such as trimethylamine and triethylamine, hydroxides, carbonates and hydrogencarbonates of sodium, potassium, lithium, calcium and ammonium and mixtures of these compounds can be used. In the industrial process, in general, sodium salts and calcium salts are used.

The amount by mole of the basic catalyst is 1.0 to 2.0 times as much as the amount by mole of the aliphatic aldehyde used as the raw material. It is necessary that the amount be adjusted in accordance with the reaction condition so that the formation of byproducts is suppressed and the object polyol is obtained with an excellent selectivity.

In the process of the present invention, the reaction liquid is neutralized with formic acid to a pH of 6.5 to 7.0. Then, the reaction liquid is concentrated by distillation in the step of concentration and water and unreacted formaldehyde are separated. The pressure in the step of concentration is 100 to 400 kPa. When the concentration of the unreacted formaldehyde is 1% or smaller, the concentration may be conducted under a reduced pressure. The reaction liquid is concentrated so that the concentration of a salt of formic acid is adjusted in the range of 15 to 25%.

In the step of extraction, the concentrated reaction liquid is treated by extraction and the object polyol and the salt of formic acid as a byproduct are separated from each other.

The extract liquid obtained after the step of extraction contains 1,000 to 3,000 ppm of the salt of formic acid. In the step of washing with water, the extract liquid is washed with water and the salt of formic acid in the extract liquid is efficiently removed and the concentration is reduced into the range of about 50 to 300 ppm. A decanter is disposed in the tank for washing with water and the treated liquid is separated into two layers, i.e., an oil layer (an upper layer) containing the polyol and an aqueous layer (a lower layer) containing the polyol and the salt of formic acid.

The amount of water used for the washing is different depending on the type of the used extracting reagent and the condition of washing. The amount by weight of water is 0.01 to 1.0 times and preferably 0.02 to 0.1 times as much as the amount by weight of the extract liquid.

In process of the first invention, a specific aliphatic aldehyde is used for the extraction as the extracting reagent in the above steps and the extracting reagent is recovered by distillation after suitably adjusting pH of the oil layer which is separated in the step of washing with water after the extraction and contains the polyol.

The extracting reagent used in this process is an aliphatic aldehyde represented by formula (ii):

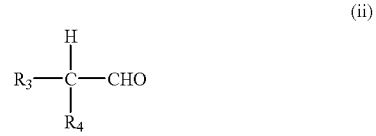

(ii)

wherein $R_3$ represents hydrogen atom or an aliphatic alkyl group having 1 or 2 carbon atoms and $R_4$ represents an aliphatic alkyl group having 1 to 5 carbon atoms Examples of the aliphatic aldehyde include NBAL, IBAL and propionaldehyde. The aliphatic aldehyde may be used as a mixture of two or more.

The amount by weight of the extracting reagent is 1.0 to 4.0 times and preferably 1.5 to 2.5 times as much as the amount by weight of the concentrated liquid. As the extractor used for the extraction, an extractor providing efficient stirring is used. A extractor of a multi-stage tank type may be used. However, the reactor of a multi-stage tank type requires many attached facilities and a single column extractor of the reciprocating-plate type is more efficient. By washing the extract liquid in a tank for washing with water disposed at the side of the outlet for the extract liquid of the extractor, the salt of formic acid can be efficiently removed.

The temperature of the extraction and the washing with water is 20 to 45° C. and preferably 25 to 35° C. When the temperature is lower than 20° C., solubility of the polyol into the extracting reagent is small. When the temperature is higher than 45° C., aldol condensation tends to take place between the aldehyde molecules used as the extracting reagent.

Since an acetal and an aldol tend to be formed as byproducts from the aldehyde used as the extracting reagent and the polyol and from the aldehyde molecules used as the extracting reagent, respectively, during recovery of the extracting reagent from the extract liquid, pH of the extract liquid is adjusted at 6.0 to 9.0 and preferably 6.5 to 8.0 to prevent the formation of the byproducts. When pH is smaller than 6.0, the acetal is formed in a great amount. When pH exceeds 9.0, the aldol condensation tends to take place between the aldehyde molecules used as the extracting reagent.

The value obtained by a pH meter in the above can also be used to evaluate the property of the extract liquid. The value of pH is essentially defined based on the concentration of hydrogen ion in an aqueous solution and used for evaluating the acidity or the basicity of an aqueous solution. However, the value of pH can be used to evaluate the acidity or the basicity as the property of the organic solution in the present invention.

To adjust pH, an alkali may be added to the reaction product liquid or the concentrated liquid supplied to the extractor. However, it is preferable that pH is adjusted in the tank for washing with water after the extraction.

The tank for washing with water described above is a tank used for washing the extract liquid with water and removing most of the salt of formic acid remaining in the extract liquid. As the alkali used for the adjustment, the basic catalyst used for the aldol condensation and the cross-Cannizzaro reaction is preferable. Hydroxides, carbonates, hydrogencarbonates and mixture of these salts are preferable.

In general, the extracting reagent is recovered in a distillation column. When the extract liquid containing the extracting reagent is supplied to the distillation column, it is preferable that the extract liquid is heated in advance for a short time in a preliminary heating tank at a temperature higher than the boiling point of the extracting reagent and then flashed into an upper portion of the distillation column so that most of the aldehyde is instantaneously vaporized. When the time of the preliminary heating is long, the amount of the acetal formed as the byproduct increases. To prevent the aldehyde from falling into lower portions of the distillation column, water or steam is supplied at a lower portion of the distillation column in an amount by weight of 0.1 to 1.0 times as much as the amount by weight of the extract liquid. The amount of the acetal formed as the byproduct can be decreased by the operation in this manner.

In the second invention, the same aliphatic aldehyde as the aliphatic aldehyde used as the raw material is used as the extracting reagent and at least a portion of the recovered extracting reagent is used as the aliphatic aldehyde of the raw material of the reaction.

The recovered extracting reagent can be used as the raw material of the reaction without any treatments and can also be used as the extracting reagent. When the recovered extracting reagent is used as the raw material of the reaction, the ratio of the amount by weight of the recovered extracting reagent to the amount by weight of the aliphatic aldehyde freshly supplied as the raw material is about 0.01 to 1 although the ratio may be different depending on the conditions and the frequency of the use.

By using as the extracting reagent the same aliphatic aldehyde as the aliphatic aldehyde used as the raw material of the reaction and by using at least a portion of the recovered extracting reagent as the raw material of the reaction as described above, accumulation of impurities in the extracting reagent can be suppressed and the efficient extraction can be achieved.

In the third invention, the aqueous layer separated in the step of washing with water is treated by distillation in the step of removing the extracting reagent and liquid obtained from the bottom of the distillation column is recycled to the step of concentration after the extracting reagent is removed or to the step of extraction after the extracting reagent and a portion of water are removed.

The aqueous layer separated in the step of washing with water contains the polyol, the salt of formic acid and some amount of the extracting reagent. When this aqueous layer is recycled to the step of concentration without any treatments, degeneration of the extracting reagent and side reactions of the extracting reagent with the polyol tend to take place. Therefore, the aqueous layer separated in the step of washing with water is distilled to remove the extracting reagent and water obtained from the bottom of the distillation column is recycled to the step of concentration.

When the aqueous layer separated in the step washing with water is recycled to the step of extraction in combination with the concentrated reaction liquid, the concentration of water in the extract liquid increases by 1 to 10% and the efficiency of extraction decreases. Therefore, the extracting reagent and a portion of water are removed from the aqueous layer separated in the step washing water by distillation in the step of removing the extracting reagent and the liquid obtained from the bottom of the distillation column is recycled to the step of extraction. In this operation, the concentration of water obtained from the distillation column from which the extracting reagent has been removed is adjusted to 20 to 80%. The pressure during the operation of removing the extracting reagent is −50 to 100 kPa.

The present invention will be described with reference to FIG. 1 in the following. FIG. 1 shows a diagram describing an example of steps in the process of the present invention. In FIG. 1, an aliphatic aldehyde as the raw material, formaldehyde and a basic catalyst are supplied to a reactor 1 via a route 2, a route 3 and a route 4, respectively, and the aldol condensation and the Cannizzaro reaction are successively conducted. The reaction product liquid is supplied to a concentration column 6 via a route 5. Formaldehyde in an excess amount and a portion of water are removed by distillation via a route 7 and a concentrated liquid is supplied to an extractor 9 via a route 8. An extracting reagent is supplied via a route 10 and a residual liquid of the extraction is removed via a route 12. An extract liquid is supplied to a tank for washing with water 13 via a route 11 and water is supplied via a route 14. In the tank for washing with water 13, the mixed extract liquid is separated into two layers in a decanter. An oil layer (an upper layer) is taken out via route 15 and supplied to a column for recovering an extracting reagent 17. An aqueous layer (a lower layer) is taken out and supplied to a column for removing an extracting reagent 18 via a route 16.

In the first invention, an alkali is added to the tank for washing with water 13 via a route 19 and pH of the oil layer is adjusted. The oil layer having the adjusted pH is supplied to the column for recovering an extracting reagent 17 via a route 15 and the extracting reagent is recovered via a route 20. The recovered extracting reagent is recycled to the extractor 9 via a route 21. The polyol separated in the column for recovering an extracting reagent 17 is transferred to a step of purification by distillation via a route 22.

In the second invention, the extracting reagent recovered in the column for recovering an extracting reagent 17 is used as the aliphatic aldehyde of the raw material of the reaction via a route 23.

In the third invention, the extracting reagent is removed from the column for recovering an extracting reagent 18 via a route 24 and a liquid taken out of the bottom of the column via a route 25 is recycled to the concentration column 6 via a route 26. Alternatively, the extracting reagent and a portion of water are removed from the column for recovering an extracting reagent 18 via a route 24 and a liquid taken out of the bottom of the column via a route 25 is recycled to the extractor 9 via a route 27.

In accordance with the process of the first invention, since the reaction product liquid is extracted with a specific aliphatic aldehyde used as the extracting reagent and the extracting reagent is recovered after pH of the extract liquid is adjusted, continuous distillation can be conducted with suppressed formation of byproducts and the high purity polyol can be obtained.

In accordance with the process of the second invention, since the same aliphatic aldehyde as the aliphatic aldehyde used as the raw material is used as the extracting reagent and the recovered extracting reagent is recycled to the reaction, accumulation of impurities (aldols, methanol, alkenals and the like) in the extracting reagent is suppressed without adverse effects on the result of the reaction and the polyol and the salt of formic acid can be efficiently separated from each other.

In accordance with the process of the third invention, since the extract liquid containing the polyol is washed with water and the washing water is recycled to the step of concentration after the extracting reagent is removed or to the step of extraction after the extracting reagent and a portion of water are removed, an efficient extraction can be achieved at a high yield of extraction of the polyol and a high fraction of the removed salt of formic acid in the step of extraction, the purification by continuous distillation can be conducted and the high quality polyol can be obtained with stability.

EXAMPLES

The present invention will be described more specifically with reference to examples in the following. However, the present invention is not limited to the examples.

In Examples and Comparative Examples, a curled column extractor of the reciprocating-plate column manufactured by SUMITOMO JUKI Co., Ltd. was used as the extractor.

In Examples and Comparative Examples, the following abbreviations are used:

NBAL: normal-butylaldehyde
TMP: trimethylolpropane
GC: gas chromatography

Example 1

The First Invention
(The Step of Reaction)

Into a reactor having a capacity of 30 liters, 7,202 g (96.0 moles) of a 40% by weight aqueous solution of formaldehyde and 8,110 g of water were placed and the resultant solution was heated at a temperature of 40° C. under stirring. Into the heated solution, 2,520 g (31.5 moles) of a 50% by weight aqueous solution of sodium hydroxide and 2,163 g (30.0 moles) of NBAL were added at a constant rate over 30 minutes. During the addition, the temperature was slowly raised from 40° C. to the maximum temperature of 60° C. and controlled at the maximum temperature. After the addition was completed, the temperature was kept at 60° C. and the reaction was allowed to continue for 15 minutes.

After the reaction was completed, the obtained reaction liquid in an amount of 20,000 g was analyzed and found to contain 17.5% by weight of TMP. The selectivity for TMP was 87.1% by mole.
(The Steps of Concentration and Extraction)

After the above reaction liquid was neutralized with formic acid to a pH of 7.0, the reaction liquid was concentrated in a pressurized distillation apparatus at a pressure of 300 kPa and the concentration was increased to twice the original concentration. The composition of the concentrated liquid was as follows: TMP: 35.0% by weight; and sodium formate: 21.4% by weight.

The concentrated liquid was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with a 0.5% by weight aqueous solution of sodium hydrogencarbonate which was supplied at a rate of 280 g/hour. The temperature inside the tank for washing with water was kept at 30° C. The extract liquid was taken out of an upper portion of a decanter attached to the tank for washing with water. A liquid at a lower portion of the decanter was taken out and supplied to the upper stage of the extractor in combination with the concentrated liquid. The flow rates of the liquids at the stationary state were as follows: the extract liquid at the top of the column of the extractor: 2,584 g/hour; the residual liquid of extraction: 656 g/hour; the extract liquid after being washed with water: 2,624 g/hour; and the liquid at the lower portion of the decanter: 240 g/hour.

The above continuous steps were continued for 15 hours and the obtained extract liquid was analyzed. The composition of the extract liquid was as follows: TMP: 13.3%; sodium formate: 80 ppm; and water: 10.3%. pH of the extract liquid was 8.5. The extract liquid contained 130 ppm of acetal and 1,500 ppm of aldol. The composition of the residual liquid of extraction was as follows: sodium formate: 32.6%; TMP: 530 ppm; and NBAL: 0.6%. The fraction of removed sodium formate was 99.9% and the yield of extracted TMP was 99.9%.

The above extract liquid was heated at 70° C. in a preliminary heating apparatus and supplied under flashing into an upper stage of a distillation column for recovering the extracting reagent at a rate of 2,624 g/hour. At a lower portion of the distillation column, steam was supplied at a rate of 500 g/hour. A distillate was taken out at a rate of 2,760 g/hour and a residual liquid in the column was taken out at a rate of 364 g/hour. The amount of aldol in the distillate was 0.14% (1.25% based on the amount of TMP). The amount of acetal in the residual liquid in the column was 0.24% based on the amount of NBAL used as the raw material. "The amount based on the amount of NBAL used as the raw material" means the amount of NBAL consumed for producing acetal per the total amount of NBAL used as the raw material. The residual liquid in the column was purified by continuous distillation and a high purity TMP having a purity of 99.9% as measured in accordance with GC was obtained at a yield of 98%.

Comparative Example 1

The concentrated liquid obtained in Example 1 was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring without using an aqueous solution of sodium hydrogencarbonate in combination with water which was supplied at a rate of 280 g/hour.

The temperature inside the tank for washing with water was kept at 30° C. The extract liquid was taken out of an upper portion of a decanter attached to the tank for washing with water. A liquid at a lower portion of the decanter was taken out and supplied to the upper stage of the extractor in combination with the concentrated liquid. The flow rates of the liquids at the stationary state were as follows: the extract liquid at the top of the column of the extractor: 2,584 g/hour; the residual liquid of extraction: 656 g/hour; the extract liquid after being washed with water: 2,624 g/hour; and the liquid at the lower portion of the decanter: 240 g/hour.

The above continuous processes were continued for 15 hours and the obtained extract liquid was analyzed. The composition of the extract liquid was as follows: TMP: 13.0%; sodium formate: 130 ppm; and water: 10.6%. pH of the extract liquid was 4.5. The extract liquid contained 5,100 ppm of acetal and 3,200 ppm of aldol.

The above extract liquid was supplied to an upper stage of a distillation column for recovering the extracting reagent a rate of 2,624 g/hour. A distillate was taken out at rate of 2,206 g/hour and a residual liquid in the column was taken out at a rate of 418 g/hour. The amount of aldol in the distillate was 0.25% (2.23% based on the amount of TMP). The amount of acetal in the residual liquid in the column was 15.3% based on the amount of NBAL used as the raw material.

Comparative Example 2

The concentrated liquid obtained in Example 1 was treated by continuous extraction using the extractor. The concentrated liquid as the liquid for extraction was supplied to an upper stage of the extractor at a rate of 1,000 g/hour and methyl isopropyl ketone as the extracting reagent was supplied to a lower stage of the extractor at a rate of 2,000 g/hour. The temperature inside the extractor was controlled at 50° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with water containing no alkali which was supplied at a rate of 280 g/hour. The temperature inside the tank for washing with water was kept at 60° C. The extract liquid was taken out of an upper portion of a decanter attached to the tank for washing with water. A liquid at a lower portion of the decanter was taken out and supplied to the upper stage of the extractor in combination with the concentrated liquid. The flow rates of the liquids at the stationary state were as follows: the extract liquid at the top of the column of the extractor: 2,564 g/hour; the residual liquid of extraction: 676 g/hour; the extract liquid after being washed with water: 2,604 g/hour; and the liquid at the lower portion of the decanter: 240 g/hour.

The above continuous processes were continued for 15 hours and the obtained extract liquid was analyzed. The composition of the extract liquid was as follows: TMP: 13.1%; sodium formate: 130 ppm; and water: 10.3%.

The above extract liquid was supplied to an upper stage of a distillation column for recovering the extracting reagent at a rate of 2,604 g/hour. A distillate was taken out at a rate of 2,181 g/hour and a residual liquid in the column was taken out at a rate of 423 g/hour. The amount of sodium formate in the residual liquid in the column was 0.78%. To 1,000 g of the residual liquid in the column, 5.9 g of phosphoric acid was added and the resultant mixture was heated at 150° C. at a pressure of 10 kPa or lower for 2 hours and sodium formate was deactivated. The treated liquid was distilled in accordance with a batch process and TMP having a purity of 97.5% as measured in accordance with GC was obtained at a yield of 86%.

Example 2

The Second Invention
(The First Reaction)

Into a reactor having a capacity of 30 liters, 7,202 g (96.0 moles) of a 40% by weight aqueous solution of formaldehyde and 8,110 g of water were placed and the resultant solution was heated at a temperature of 40° C. under stirring. Into the heated solution, 2,520 g (31.5 moles) of a 50% by weight aqueous solution of sodium hydroxide and 2,163 g (30.0 moles) of NBAL were added at a constant rate over 30 minutes. During the addition, the temperature was slowly raised from 40° C. to the maximum temperature of 60° C. and controlled at the maximum temperature. After the addition was completed, the temperature was kept at 60° C. and the reaction was allowed to continue for 15 minutes.

After the reaction was completed, the obtained reaction liquid in an amount of 20,000 g was analyzed and found to contain 17.5% by weight of TMP. The yield of TMP was 87.1% by mole.

After the above reaction liquid was neutralized with formic acid to a pH of 7.0, the reaction liquid was concentrated in a pressurized distillation apparatus at a pressure of 300 kPa and the concentration was adjusted to twice the original concentration.

The concentrated liquid was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with a 0.5% by weight aqueous solution of sodium hydrogencarbonate which was supplied at a rate of 280 g/hour. The temperature inside the tank for washing with water was kept at 30° C. The extract liquid was taken out of an upper portion of a decanter attached to the tank for washing with water. A liquid at a lower portion of the decanter was taken out and supplied to the upper stage of the extractor in combination with the concentrated liquid. The flow rates of the liquids at the stationary state were as follows: the extract liquid at the top of the column of the extractor: 2,584 g/hour; the residual liquid of extraction: 656 g/hour; the extract liquid after being washed with water: 2,624 g/hour; and the liquid at the lower portion of the decanter: 240 g/hour.

The composition of the residual liquid of extraction was as follows: sodium formate: 32.6%; and TMP: 530 ppm. The composition of the extract liquid was as follows: TMP: 13.3%; sodium formate: 80 ppm; and water: 10.7%. The fraction of removed sodium formate was 99.9% and the yield of the extracted TMP was 99.9%.

The obtained extract liquid after being washed with water was supplied to an upper stage of the distillation column for recovering the extracting reagent at a rate of 2,624 g/hour and a distillate and a residual liquid in the column were taken out at rates of 2,260 g/hour and 364 g/hour, respectively. The distillate (the recovered extracting reagent) contained 0.14% of NBAL aldol, 0.02% of methanol and 0.03% of 2-alkenal.

(The Second Reaction)

Into a reactor having a capacity of 30 liters, 7,207 g (96.0 moles) of a 40% by weight aqueous solution of formaldehyde and 8,110 g of water were placed and the resultant solution was heated at a temperature of 40° C. under stirring. Into the heated solution, 2,520 g (31.5 moles) of a 50% by weight aqueous solution of sodium hydroxide, 1,947 g (27.0 moles) of NBAL and 225.3 g (NBAL: 96%; water: 4%) of the recovered extracting reagent obtained in the first reaction were added at a constant rate over 30 minutes. During the addition, the temperature was slowly raised from 40° C. to the maximum temperature of 60° C. and controlled at the maximum temperature. After the addition was completed, the temperature was kept at 60° C. and the reaction was allowed to continue for 15 minutes. The amount of the recovered extracting reagent used in this reaction relative to the amount of NBAL as the fresh raw material was 10% by weight.

After the reaction was completed, the obtained reaction liquid in an amount of 20,009 g was analyzed and found to contain 17.4% by weight of TMP. The yield of TMP was 86.8% by mole.

The reaction and the extraction were repeated 10 times in accordance with the procedures described above. The extracting reagent obtained after the tenth extraction contained 0.18% of NBAL aldol, 0.02% of methanol and 0.02% of 2-alkenal. No accumulation of impurities was found. The fraction of removed sodium formate was 99.9 and the yield of the extracted TMP was 99.9%.

Comparative Example 2

The same procedures as those conducted in Example 2 were conducted except that the recovered extracting agent was not used as the raw material but used as the extracting reagent 10 times repeatedly. The extracting reagent obtained after the tenth extraction contained 1.65% of NBAL aldol, 0.22% of methanol and 0.25% of 2-alkenal. The fraction of removed sodium formate was 98.7 and the yield of the extracted TMP was 98.5%.

Example 3

The Third Invention

After the reaction liquid obtained in the step of reaction of Example 1 was neutralized with formic acid to a pH of 7, the neutralized reaction liquid was supplied to a pressurized distillation apparatus at a rate of 2,000 g/hour and concentrated at 300 kPa so that the volume of the concentrated solution was ½ of the reaction liquid.

The concentrated liquid was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with a 0.5% by weight aqueous solution of sodium hydrogencarbonate which was supplied at a rate of 280 g/hour. The temperature inside the tank for washing with water was kept at 30° C.

An extract liquid was taken out of an upper portion of a decanter attached to the tank for washing with water. A liquid at a lower portion of the decanter was taken out. The flow rates of the liquids at the stationary state were as follows: the extract liquid at the top of the column of the extractor: 2,544 g/hour; the residual liquid of extraction: 656 g/hour; the extract after being washed with water: 2,584 g/hour; and the liquid at the lower portion of the decanter: 240 g/hour.

The liquid taken out of the lower portion of the decanter was supplied to a five-stage distillation column. A distillate and a residual liquid in the column were taken out at rates of 40 g/hour and 200 g/hour, respectively. The residual liquid in the column was recycled to the pressurized distillation apparatus in the step of concentration and concentrated in combination with the reaction solution.

The above procedures were continued for 5 hours and the extract liquid and the residual liquid after the extraction were analyzed. The composition of the extract liquid was as follows: TMP: 13.3%; sodium formate: 80 ppm; and water: 10.7%. The composition of the residual liquid of extraction was as follows: sodium formate: 32.6%; and TMP: 530 ppm. The fraction of the removed sodium formate was 99.9% and the yield of the extracted TMP was 99.9%.

Comparative Example 3

After the reaction liquid obtained in the step of reaction of Example 1 was neutralized with formic acid to a pH of 7, the neutralized reaction liquid was supplied to a pressurized distillation apparatus at a rate of 20,000 g/hour and concentrated at 300 kPa so that the volume of the concentrated solution was ½ of the reaction liquid.

The concentrated liquid was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with a 0.5% by weight aqueous solution of sodium hydrogencarbonate which was supplied at a rate of 280 g/hour. The temperature inside the tank for washing with water was kept at 30° C. An extract liquid was taken out of an upper portion of a decanter attached to the tank for washing with water. A liquid at a lower portion of the decanter was taken out and supplied to the upper stage of the extractor in combination with the concentrated liquid. The flow rates of the liquids at the stationary state were as follows: the extract liquid at the top of the column of the extractor: 2,584 g/hour; the residual liquid of extraction: 656 g/hour; the extract liquid after being washed with water: 2,624 g/hour; and the liquid at the lower portion of the decanter: 240 g/hour.

The above procedures were continued for 5 hours and the extract liquid and the residual liquid after the extraction were analyzed. The composition of the extract liquid was as follows: TMP: 13.1%; sodium formate: 900 ppm; and water: 10.3%. The composition of the residual liquid of extraction was as follows: sodium formate: 31.3%; and TMP: 1.26%. The fraction of the removed sodium formate was 98.9% and the yield of the extracted TMP was 97.5%. Due to the great content of sodium formate, the crude TMP obtained after removing the extracting reagent from the extract liquid could not be purified by continuous distillation.

In the present Comparative Example, since the lower layer of the decanter was recycled to the step of extraction without removing the extracting reagent, the material for extraction was diluted. Therefore, the step of extraction became unstable and the content of sodium formate remaining in the extracting reagent increased. It was also found that the amount of TMP mixed into the sodium formate in the residual liquid of extraction increased.

Example 4

After the reaction liquid obtained in the step of reaction of Example 1 was neutralized with formic acid to a pH of 7, the neutralized reaction liquid was supplied to a pressurized distillation apparatus at a rate of 2,000 g/hour and concentrated at 300 kPa so that the volume of the concentrated solution was ½ of the reaction liquid.

The concentrated liquid was treated by continuous extraction using the extractor. The concentrated liquid as the liquid for extraction was supplied to an upper stage of the extractor at a rate of 1,000 g/hour and NBAL as the extracting reagent was supplied to a lower stage of the extractor at a rate of 2,000 g/hour. The temperature inside the extractor was controlled at 30° C. An extract liquid was taken out of the top of the column of the extractor and a residual liquid of extraction was taken out of the bottom of the column of the extractor. The obtained extract liquid was supplied to a tank for washing with water having a capacity of 1 liter under stirring in combination with a 0.5% by weight aqueous solution of sodium hydrogencarbonate which was supplied at a rate of 280 g/hour. The temperature inside the tank for washing with water was kept at 30° C. The extract liquid was taken out of an upper portion of a decanter attached to the tank for washing with water. A liquid at a lower portion of the decanter was taken out. The flow rates of the liquids at the stationary state were as follows: the extract liquid at the top of the column of the extractor: 2,379 g/hour; the residual liquid of extraction: 656 g/hour; the extract residual liquid after being washed with water: 2,419 g/hour; and the liquid at the lower portion of the decanter: 240 g/hour.

The liquid taken out of the lower portion of the decanter was supplied to a five-stage distillation column and a distillate and a residual liquid in the column were taken out at rates of 205 g/hour and 35 g/hour, respectively. The residual liquid in the column was supplied to the upper stage of the extractor in combination with the concentrated liquid.

The above procedures were continued for 5 hours and the extract liquid and the residual liquid after the extraction were analyzed. The composition of the extract liquid was as follows: TMP: 13.3%; sodium formate: 80 ppm; and water: 10.7%. The composition of the residual liquid of extraction was as follows: sodium formate: 32.6; and TMP: 530 ppm. The composition of the residual liquid in the distillation column was as follows: TMP: 41.1%; sodium formate: 13.7%; and water: 45.2%. The fraction of the removed sodium formate was 99.9% and the yield of extracted TMP was 99.9%.

What is claimed is:

1. A process for producing a polyol by reacting an aliphatic aldehyde represented by formula (i):

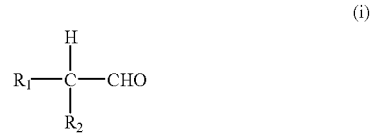

wherein $R_1$ and $R_2$ each represent hydrogen atom or an aliphatic alkyl group having 1 to 6 carbon atoms, with formaldehyde in a presence of a basic catalyst, which process comprises (1) a step of concentration which comprises removing water and unreacted formaldehyde from a reaction liquid by distillation; (2) a step of extraction which comprises extracting the polyol from a concentrated reaction liquid with an extracting reagent; and (3) a step of washing with water which comprises washing an extract liquid with water and separating the liquid into an oil layer containing the polyol and an aqueous layer; wherein an aliphatic aldehyde represented by formula (ii):

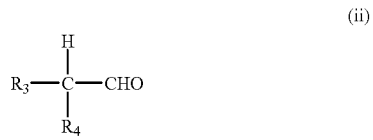

wherein $R_3$ represents hydrogen atom or an aliphatic alkyl group having 1 or 2 carbon atoms and $R_4$ represents an aliphatic alkyl group having 1 to 5 carbon atoms is used as the extracting reagent, and the extracting reagent is recovered after adjusting pH of the oil layer containing the polyol which is separated in the step of washing with water, the pH being adjusted in a range of 6.0 to 9.0.

2. A process for producing a polyol according to claim 1, wherein the pH is adjusted in the range of 6.0 to 9.0 in the step of washing with water.

3. A process for producing a polyol according to claim 2, wherein the basic catalyst is used for adjusting pH in the step of washing with water.

4. A process for producing a polyol according to claim 2, wherein, when the extracting reagent is recovered from the oil layer, the oil layer is preliminarily heated in advance and flashed into an upper stage of a distillation column.

5. A process for producing a polyol according to claim 2, wherein the extracting reagent is recovered from the oil layer while water or steam is introduced into a bottom portion of a distillation column.

6. A process for producing a polyol according to claim 2, wherein a same aliphatic aldehyde as the aliphatic aldehyde used as a raw material of the reaction is used as the extracting reagent and at least a portion of the recovered extracting reagent is used as the raw material.

7. A process for producing a polyol according to claim 6, wherein the recovered extracting reagent is used in an amount such that a ratio of the amount by weight of the recovered extracting reagent to an amount by weight of the aliphatic aldehyde freshly supplied as the raw material is in a range of 0.1 to 1.

8. A process for producing a polyol according to claim 2, wherein the extract liquid is washed with water in the step of washing with water, the extracting reagent in a separated aqueous layer using a decanter is removed by distillation and water obtained from a bottom of a distillation column in the distillation is recycled to the step of concentration.

9. A process for producing a polyol according to claim 2, wherein the extract liquid is washed with water in the step of washing with water, the extracting reagent and a portion of water in a separated aqueous layer using a decanter are removed by distillation and a liquid obtained from a bottom of a distillation column in the distillation is recycled to the step of extraction.

10. A process for producing a polyol according to claim 9, wherein the liquid obtained from the bottom of a distillation column and recycled to the step of extraction has a concentration of water in a range of 20 to 80% by weight.

11. A process for producing a polyol according to claim 1, wherein the pH is adjusted in the range of 6.5 to 8.0.

12. A process for producing a polyol according to claim 1, wherein the pH is adjusted by adding an alkali.

13. A process for producing a polyol according to claim 12, wherein said alkali added to adjust pH is a same material as said basic catalyst.

* * * * *